(12) United States Patent
Pauletti et al.

(10) Patent No.: US 7,939,098 B2
(45) Date of Patent: *May 10, 2011

(54) COMPOSITIONS AND METHOD FOR TRANSMUCOSAL DRUG DELIVERY AND CRYOPROTECTION

(75) Inventors: Giovanni M. Pauletti, Loveland, OH (US); James H. Liu, University Heights, OH (US); Wolfgang A. Ritschell, Cincinnati, OH (US)

(73) Assignee: Femina Pharma Incorporated, Miami, FL (US)

( * ) Notice: Subject to any disclaimer, the term of this patent is extended or adjusted under 35 U.S.C. 154(b) by 1098 days.

This patent is subject to a terminal disclaimer.

(21) Appl. No.: 10/444,634

(22) Filed: May 22, 2003

(65) Prior Publication Data

US 2003/0219472 A1 Nov. 27, 2003

Related U.S. Application Data

(60) Provisional application No. 60/382,644, filed on May 23, 2002.

(51) Int. Cl.
*A61K 38/00* (2006.01)
*A61K 38/01* (2006.01)

(52) U.S. Cl. .................. 424/434; 424/443; 424/430

(58) Field of Classification Search .................. None
See application file for complete search history.

(56) References Cited

U.S. PATENT DOCUMENTS

| | | | | |
|---|---|---|---|---|
| 4,948,588 A * | 8/1990 | Kamiya et al. | ................ | 424/436 |
| 5,204,108 A * | 4/1993 | Illum | ............................ | 424/434 |
| 5,346,701 A * | 9/1994 | Heiber et al. | ................. | 424/435 |
| 5,482,706 A * | 1/1996 | Igari et al. | .................... | 424/85.7 |
| 5,578,567 A * | 11/1996 | Cardinaux et al. | .............. | 514/12 |
| 5,985,313 A | 11/1999 | Neurath et al. | | |
| 6,019,988 A * | 2/2000 | Parab et al. | .................... | 424/400 |
| 6,086,909 A * | 7/2000 | Harrison et al. | ............... | 424/430 |
| 6,103,266 A * | 8/2000 | Tapolsky et al. | .............. | 424/484 |
| 6,143,278 A | 11/2000 | Elkhoury | | |
| 6,241,969 B1 | 6/2001 | Saidi et al. | | |
| 6,416,779 B1 * | 7/2002 | D'Augustine et al. | ........ | 424/430 |
| 6,495,160 B2 | 12/2002 | Esposito et al. | | |
| 2003/0219440 A1 * | 11/2003 | Tobia et al. | ................ | 424/146.1 |

OTHER PUBLICATIONS

Aungst, et al., Comparison of Nasal, Rectal, Buccal, Sublingual and Intramuscular Insulin Efficacy and the Effects of a Bile Salt Absorption Promoter, *Journal of Pharmacology and Experimental Therapeutics*, 244/1:23-27 (Jan. 1, 1987).

Sinha, et al., Permeation Enhancers for Transdermal Drug Delivery, *Drug Development and Industrial Pharmacy*, 26/11:1131-1140 (2000).

Bouwstra, et al., The Skin Barrier in Healthy and Diseased State, ScienceDirect, *Biochemica et Biophysica Acta*, 1758:2080-2095, (2006).

Palm, et al., Effect of Molecular Charge on Intestinal Epithelial Drug Transport: pH-Dependent Transport of Cationic Drugs, *The Journal of Pharmacology and Experimental Therapeutics*, 291/2:435-443 (Jun. 2, 1999).

* cited by examiner

*Primary Examiner* — Robert A Wax
*Assistant Examiner* — Melissa S Mercier
(74) *Attorney, Agent, or Firm* — Antonelli, Terry, Stout & Kraus, LLP.

(57) ABSTRACT

Compositions and methods for vaginal, buccal or nasal transmucosal delivery of drugs and for cryoprotecting of cells and embryos. For cryoprotection, the composition consisting essentially consist of a non-ionizable glycol derivative. For transmucosal delivery, the compositions essentially consist of a non-ionizable glycol derivative in a combination with a pharmaceutically active agent. For transmucosal delivery, the non-ionizable glycol derivative may be further combined with a mucoadhesive agent and/or a penetration enhancer and/or lipophilic or hydrophilic carrier for adhesion to and transport through a mucosa. The compositions are particularly suitable for administration of drugs through a nasal, buccal and vaginal mucosa or for long-term preservation of cell or embryos.

21 Claims, 2 Drawing Sheets

COMPOSITIONS AND METHOD FOR TRANSMUCOSAL DRUG DELIVERY AND CRYOPROTECTION

BACKGROUND OF THE INVENTION

1. Field of the Invention

The present invention concerns pharmaceutically acceptable compositions and methods for transmucosal delivery of drugs and for cryoprotection of cells, tissues, organs and embryos. In particular, the invention concerns the compositions consisting essentially of a non-ionizable glycol derivative for cryoprotection and a non-ionizable glycol derivative in combination with a pharmaceutically active agent for transmucosal delivery. For transmucosal delivery, the non-ionizable glycol derivative may be further combined with a mucoadhesive agent and/or a penetration enhancer and/or lipophilic or hydrophilic carrier for adhesion to and transport through a mucosa. The compositions of the invention are particularly suitable for administration of therapeutic and/or palliative drugs through a nasal, buccal or vaginal mucosa or for long-term preservation of cell, tissues, organs or embryos.

2. Background of the Invention and Related Disclosures

The skin and mucous membranes such as those that line the vagina or nasal and buccal cavity, serve as a protective barrier against the outside environment such that bacteria and viruses, chemicals and other non-native substances are excluded and prevented from entering the body through these routes. Besides excluding harmful bacteria and viruses, the above described barriers are also very effective at excluding chemicals, drugs and pharmaceutical agents that are applied to the skin or to the mucosa. These barriers are composed of several layers.

The skin is composed of keratin, epidermis, dermis and basement membrane layers. In the skin, keratin represents a cornified layer, epidermis is formed of a layer of stratified squamous epithelial cells, dermis is formed of a thin layer of cells that interdigitates with the epidermis and a basement membrane covers the capillary plexus leading to the systemic circulation.

Mucosa, similarly to the skin, is lined by multiple layers of stratified, squamous epithelium cells that form a protective barrier for exclusion of bacteria, viruses, chemicals and other substances to the organism.

Because of this mucosal barrier, nasal, buccal or vaginal medications are known to be poorly, or not at all, absorbed into the systemic circulation and their therapeutic effect is confined primarily to the external or internal topical use, as in a case of vaginal antimycotics or nasal creams or gels.

In order to permit drugs to pass through the skin barrier, attempts were made to develop permeation enhancers. Of these enhancers, the most well known is dimethyl sulfoxide (DMSO). DMSO has the ability to rapidly alter the cell membrane characteristics to allow substances to pass between the cells, into the cell and through the cells. These unique characteristics have made this compound useful in the laboratory as a permeation enhancer and as a cryoprotectant for cell freezing. Unfortunately DMSO is not safe for human use and has been banned for human use by the Food and Drug Administration.

A second skin permeation enhancer, ethoxydiglycol, known under its trade name TRANSCUTOL®, has been recently developed and introduced for topical use. This enhancer has, until now, been primarily used to promote delivery of skin tanning agents into the epidermis and into the dermal layer of the skin.

In vitro evaluation of ethoxydiglycol as permeation enhancer for transdermal delivery of clonazepam is described in *European J. Pharm. Sci.,* 9:365-372 (2000). This publication evaluates the penetration enhancing effect of ethoxydiglycol alone or in combination with propylene glycol, on clonazepam permeation through an artificial membrane made of carbopol hydrogels and through excised (ex vivo) rabbit ear skin. The article describes an increase of drug permeation through the skin as a function of ethoxydiglycol content in the formulation, and concludes that, when combined with propylene glycol which has penetration and carrier properties, ethoxydiglycol is a good enhancing carrier for clonazepam and increases the flux of the drug into the skin and across the skin.

Until recently, however, this compound has not been used for or shown to promote the transmucosal delivery of the drug across the nasal, buccal and vaginal mucosa into the systemic circulation or described to have such properties. Prior use of ethoxydiglycol to promote transvaginal delivery was by inventors and such use is described in U.S. Pat. Nos. 6,086,909 and 6,197,327, 6,416,779 and 6,572,874.

Thus, it would be advantageous to have available other penetration enhancers and compositions which would promote a transfer of pharmaceutical agents through the nasal, buccal and vaginal mucosal membranes and deliver pharmacologically active agents through these tissues into the systemic blood circulation.

Transvaginal compositions for delivery of drugs to the uterus through vaginal mucosa have been recently discovered and described in U.S. Pat. Nos. 6,086,909 and 6,197,327 B1. These compositions typically consist of a permeation enhancer or sorption promoter, such as diglycol, interesterified stone oil, bile salt etc., mucoadhesive agent and, depending on the drug properties, either a lipophilic or a hydrophilic carrier.

It has now been discovered that a presence of a non-ionizable glycol derivative promotes and permits transmucosal drug delivery through a nasal, buccal and vaginal mucosa into the general blood circulation.

It is therefore an object of the present invention to provide compositions and methods for transmucosal delivery of effective doses of pharmaceutical agents to the general circulation.

All patents, patent applications and publications cited herein are hereby incorporated by reference.

SUMMARY OF THE INVENTION

One aspect of the present invention is a composition which promotes an effective transmucosal delivery of pharmaceutical agents through nasal, buccal or vaginal mucosa into a systemic blood circulation.

Another aspect of the current invention is a pharmaceutically acceptable composition which promotes effective transmucosal drug delivery, said compositions consisting essentially of a non-ionizable glycol derivative.

Still another aspect of the current invention is a pharmaceutically acceptable composition consisting essentially of a non-ionizable glycol derivative in a combination with a pharmaceutically active agent.

Still yet another aspect of the current invention is a composition consisting essentially of a non-ionizable glycol derivative alone or in combination with another penetration enhancer and/or mucoadhesive agent and/or lipophilic or hydrophilic carrier in combination with a pharmaceutically active agent.

Still yet another aspect of the current invention is a transmucosal composition for delivery of an active pharmaceutically acceptable agent through nasal, buccal or vaginal mucosa, said composition consisting essentially of about 0.01 to about 60%, preferably from about 5 to about 20%, of ethoxydiglycol or another non-ionizable glycol, said composition formulated as a solution, suspension, emulsion, gel, lotion, spray, tablet, dissolvable tablet for buccal use, ointment or foam for administration thereof alone or incorporated into a device for insertion into nasal, buccal or vaginal cavity.

Yet another aspect of the current invention is a cryoprotective formulation for cryoprotection of cells or embryos, said composition comprising a non-ionizable glycol derivative alone or in combination with another solvent, such as propanediol, for long-term preservation of cells and embryos.

DEFINITIONS

As used herein:

"DMSO" means dimethyl sulfoxide.

"TRANSCUTOL®" means ethoxydiglycol also known under the name of diethyleneglycol monoethyl ether.

"Agent", "pharmaceutically acceptable agent", "pharmaceutical agent", "an active pharmaceutically acceptable agent" or "drug" means a natural or synthetic chemical compound which asserts a therapeutic effect when administered to a mammal, including human subject, through the mucosa, and which is a polar substance having an octanol/water partition coefficient (log p) smaller than 2.5 (<2.5).

"Non-ionizable glycol derivative" means a synthetic or non-naturally occurring conjugate of aliphatic glycol or a conjugate of aliphatic glycol with aliphatic or aromatic alcohol or ester, such as ethoxydiglycol known under its trade name TRANSCUTOL®, or mixtures thereof.

DETAILED DESCRIPTION OF THE INVENTION

The current invention describes compositions and methods suitable for transmucosal delivery of drugs across nasal, buccal and vaginal mucosa into general systemic blood circulation and for long-term preservation of cells, tissues, organs or embryos.

The compositions of the invention permit efficacious delivery of pharmaceutically active agents directly into the general systemic circulation through the nasal, buccal or vaginal mucosa. Such route of delivery eliminates a need for large drug doses and also a drug deactivation connected with the oral drug delivery, or invasive routes of drug administration, such as intravenous, intramuscular, intraperitoneal, cutaneous or subcutaneous injections requiring visit to the doctor's office and/or assistance of medical personnel.

The currently described route of transmucosal administration is noninvasive, requires no assistance by medical personnel or visit to the doctor's office, eliminates the need for administration of excessive doses of the drug needed for the oral delivery, and is altogether more convenient, practical and economical. The transmucosal delivery of the drugs according to the invention bypasses the gastrointestinal tract absorption, liver metabolism and kidney deactivation and delivers the drug directly to the systemic blood circulation.

Moreover, the compositions of the invention promote and permit delivery of the drug with variable chemical properties, such as variable drug stability, solubility and absorption into the tissue. The novel route of drug delivery eliminates side effects observed with oral administration of higher doses of the drug, because this route delivers the drug directly to the blood circulation through the utilization of a mucosal penetration enhancer alone or in combination with appropriate lipophilic or hydrophilic carrier and/or mucoadhesive agent, depending on the drug.

A second utility of the current compositions is a non-ionizable glycol derivative cell protective effect during long-term protection of cells, tissue, embryos or organs. The rapid penetration of a non-ionizable glycol derivative into the cells displaces the water fraction within the cells and permits the glycol derivative to act as a cryoprotectant.

I. Transmucosal Compositions

Transmucosal compositions of the invention consists essentially of a non-ionizable glycol derivative.

A. Non-ionizable Glycol Derivatives

A non-ionizable glycol derivative is a synthetic or non-naturally occurring conjugate of aliphatic glycol or a conjugate of aliphatic glycol with aliphatic or aromatic alcohol or ester. The non-ionizable glycol derivative is typically present in the transmucosal composition in an amount from about 0.01 to about 60%, preferably from about 5 to about 25%, most preferably from about 10 to about 15%, by weight.

Representative permeation enhancers include but are not limited to compounds listed in following sections 1 (a-c), 2 (a-e) and 3(a). The most preferred non-ionizable glycol derivative is ethoxydiglycol, also known as TRANSCUTOL®, commercially available from Gattefosse, Westwood, N.J.

1. Non-Ionizable Glycol Ether Derivatives

A non-ionizable glycol ether derivative is a polyoxyethylene alkyl ether, ester or a glycol derivative with glycerol ester represented by a compound selected from the group consisting of:

a. polyoxyethylene alkyl ether such as, for example, polyoxyethylene lauryl ether, polyoxyethylene monooleyl ether and ethoxydiglycol;

b. polyoxyethylene alkyl phenol, such as, for example polyoxyethylene nonylphenol and polyoxyethylene octylphenol ether;

c. polyoxyethylene sterol, such as, for example polyoxyethylene cholesterol ether and polyoxyethylene soya sterol ether.

2. Non-Ionizable Glycol Ester Derivatives

A non-ionizable glycol ester derivative is a polyoxyethylene glycol ester, polyoxyethylene glycerol fatty acid ester, polyoxyethylene glyceride or polyoxyethylene vegetable or hydrogenated oil, said derivative represented by a compound selected from the group consisting of:
  a. polyoxyethylene glycol ester, such as, for example, polyoxyethylene monooleate, polyoxyethylene dilaurate, polyoxyethylene mono and dioleate;
  b. polyoxyethylene glycerol fatty acid ester, such as, for example, polyoxyethylene glyceryl laurate and polyoxyethylene glyceryl oleate;
  c. polypropylene glycol fatty acid ester, such as, for example, propylene glycol oleate and propylene glycol stearate;
  d. polyoxyethylene glyceride, such as, for example, polyoxyethylene sorbitan monooleate and polyoxyethylene tristearate;
  e. polyoxyethylene vegetable or hydrogenated oil, such as, for example, polyoxyethylene hydrogenated castor oil, polyoxyethylene almond oil, polyoxyethylene apricot kernel oil, polyoxyethylene caprylic or capric glycerides, lauroyl macrogol glycerides, oleoyl macrogol-6-glyceride, linoleoyl macrogol-6-glycerides, and polyoxyethylated glycolysed glycerides.

3. Glycol Derivatives with Glycerol Esters

A non-ionizable glycol derivative with glycerol ester is represented by a compound:
  a. glycol derivative with glycerol ester, such as, for example, polyoxyethylene oleate and polyoxyethylene glyceryl stearate.

4. Transmucosal Compositions

The compositions of the invention comprises at least one or a mixture of two or several non-ionizable glycol derivatives and an active pharmaceutically acceptable agent and may also additionally include a penetration enhancer or sorption promoter, a mucoadhesive compound, a carrier and/or inactive pharmaceutically acceptable excipient.

The additional penetration enhancer or sorption promoter may be added to further enhance permeation of the drug(s) across the nasal, buccal or vaginal barrier. Preferred sorption promoters include non-ionic surface active agents, bile salts, organic solvents, chelators, cyclodextrins or fatty acids.

B. Solubilizing and Penetration Enhancing Properties of Non-Ionizable Glycol Derivatives The non-ionizable glycol derivatives of the invention are the amphiphilic surfactants acting as penetration enhancers having the ability to interact with important regulatory proteins at cell-cell connections, that is to form tight cell-cell junctions. As a result, there is an increase in aqueous pore between adjacent cells which leads to enhanced flux of hydrophilic molecules (i.e. penetration enhancing effect via the paracellular route). In addition, surfactants perturb the bilayer environment of biological membranes. Increased membrane fluidity that is facilitated by incorporation of surfactants such as non-ionizable glycol derivatives enhance the flux of lipophilic drug molecules (i.e. permeation enhancing effect via the transcellular route). Ultimately, amphiphilic surfactants facilitate the interaction between lipophilic molecules and aqueous environment. This increases the aqueous solubility of the drug molecule and, simultaneously, promotes transport of an greater mass fraction per time unit across the membrane barrier (i.e. penetration enhancing effect via solubility increase).

C. Additional Composition Components

In order to achieve desirable drug release from the transmucosal composition, the active ingredient is optionally incorporated into a vehicle or carrier for which the drug has low affinity. Hence, hydrophilic drugs are incorporated into lipophilic carriers, and lipophilic drugs are incorporated into hydrophilic carriers.

Preferred lipophilic carriers for use with hydrophilic drugs include mixtures of triglycerides of a higher saturated fatty acids, particularly the fatty acid from C8 to C18 carbon chain, along with varying proportions of mono- and diglycerides. Special grade carriers may contain additives, such as lecithin, polysorbates, ethoxylated fatty alcohols, interesterified C8-C18 triglycerides and ethoxylated partial fatty glycerides, such as SUPPOCIRE® AS2 or AS2X, commercially available from Gattefosse, Westwood, N.J., WITEPSOL® H15 or W25, commercially available from Condea, Cronford, N.J., or ESTARAM® or SUPOWEISS®, commercially available from Uniqema, New Castle, Del.

Non-limiting examples of a hydrophilic carrier include polyethylene glycol having an average molecular weight (m.w.) between 200-8000, such polyethylene glycol of average m.w. of 6000, polyethylene glycol having an average mol. weight of 3350, polyethylene glycol having an average molecular weight of 1500, polyethylene glycol having an average molecular weight of 200 or mixtures thereof. Preferred hydrophilic carriers for promoting a lipophilic drug delivery include polyethylene glycol (PEG) from about 200 to about 8000 m.w., or a mixture thereof, such as PEG 6000/PEG 1500, or PEG 6000/PEG 1500, PEG 1500/PEG 400, or PEG 6000/PEG 400. Polyethylene glycols are commercially available from Sigma/Aldrich, St. Louis, Mo. Other examples of hydrophilic carriers include glycerinated gelatin, commercially available from Sigma/Aldrich, St. Louis, Mo., and polyoxyethylene glyceryl cocoate, commercially available from Protameen Chemicals, Totowa, N.J.

The system of the invention may also comprise a mucoadhesive agent to bring the drug into prolonged, close contact with the mucosal surface. The mucoadhesive agent is preferably a polymer such as an alginate, pectin, or a cellulose derivative. Hydroxypropyl methylcellulose (HPMC) is particularly preferred for use in the present invention. Other examples of mucoadhesive agents include polyacrylic acid, hyaluronic acid, polyvinyl alcohol, polyvinylpyrrolidone, polycarbophil and carbopol.

D. Specific or Preferred Compositions

Specific and preferred transmucosal compositions are those consisting essentially of from about 0.5 to about 25 wt/% of a non-ionizable glycol or a non-ionizable glycol derivative. More preferred are compositions consisting essentially from 10 to 20 wt % with the most preferred compositions consisting of about 15 wt % of ethoxydiglycol.

In a general method for preparing a composition of the invention, 0.001 to 2000 mg of the drug is dissolved in from about 0.5 to about 25% of a non-ionizable glycol derivative, preferably in about 15 wt % ethoxydiglycol, and incorporated into a device, such as an intravaginal tampon, suppository, tablet, foam, pessary, etc., or molded into a buccal dissolvable tablet, strip, spray or patch or incorporated into a foam, gel capsule or another form suitable for buccal insertion or incorporated into solution, spray suspension, a cream, gel or another form suitable for nasal application. Typically, for transvaginal delivery, the composition contains higher percentage of the glycol derivative than for nasal or buccal transmucosal delivery as the barrier properties of the nasal and buccal mucosa are less restrictive and blood supply is closer to the mucosal surface than in the vaginal mucosa.

Preferred compositions for transmucosal delivery of 0.001 to 2000 mg of hydrophilic drugs comprise between about 0.01 to about 60%, preferably about 5-20%, by weight, of a non-ionizable glycol derivative, from about 60-90% by weight lipophilic carrier, between about 0.05-25% mucoadhesive agent, and optionally between about 5-10% a sorption promoter, solubilizer or another pharmaceutically acceptable excipient.

The most preferred composition for delivery of the hydrophilic drug comprises about 5-20%, preferably about 15% wt of ethoxydiglycol, 0.1-200 mg of the drug, about 75 wt % of lipophilic carrier and about 0.5 to about 10 wt % of mucoadhesive agent for transvaginal delivery. For buccal and nasal delivery, the amount of the mucoadhesive is lower, about 0.02-7.5%, than for transvaginal delivery.

In a general method for preparing a transmucosal formulation including a hydrophilic drug, the lipophilic carrier is melted at 45-50° C. in a heated vessel. The muco-adhesive agent is added to the carrier with stirring. The hydrophilic drug is dissolved in the non-ionizable glycol derivative acting as a penetration enhancer or sorption promoter, and the drug/sorption promoter solution is added to the carrier/mucoadhesive agent solution. The final formulation is poured into molds of the desired size and shape or incorporated into a solution, suspension, cream, ointment, foam, dissolvable buccal tablet or strip, or incorporated into an intravaginal or other suitable device.

Preferred formulations for lipophilic drugs comprise 0.001-2000 mg of the drug, about 0.01 to about 60% of non-ionizable glycol derivative, preferably 5-25%, between about 50 and about 90% hydrophilic carrier, between about 5-20% mucoadhesive agent, and optionally between about 5-10% of another sorption promoter or another pharmaceutically acceptable excipient.

The most preferred composition for delivery of the lipophilic drug comprises about 5 to about 20% wt of ethoxydiglycol, 0.1-200 mg of the drug, about 75 wt % of hydrophilic carrier and about 10 wt % of mucoadhesive agent for transvaginal delivery. For buccal and nasal delivery, the amount of the mucoadhesive is lower than for transvaginal delivery.

In a general method for preparing a formulation including a lipophilic drug, the hydrophilic carrier is melted in a heated vessel at an appropriate temperature for the particular polyethylene glycol (PEG) used. The mucoadhesive agent is added to the carrier with stirring. The preferred lipophilic drug is dissolved in the sorption promoter, and the drug/sorption promoter solution is added to the carrier/mucoadhesive agent solution. The final formulation is poured into molds or pressed into structures of the desired size and shape or incorporated into a solution, suspension, cream, ointment, foam, dissolvable buccal tablet or capsule or incorporated into an intravaginal or other device.

In one embodiment of the invention, the formulation comprises from 5-20% of non-ionizable glycol derivative, about 75-85%, by weight, lipophilic carrier, about 10-15% mucoadhesive agent, by weight, and optionally, between about 5-10%, by weight, another penetration enhancer acting as a solubilizer.

In another embodiment of the invention, the formulation comprises from 5-20%, by weight, of a non-ionizable glycol derivative, about 75-85%, by weight, hydrophilic carrier, about 10-15% mucoadhesive agent, and optionally, between about 5-10%, by weight, another penetration enhancer acting as a solubilizer.

In another embodiment, the formulation additionally comprises a pharmaceutically acceptable biocompatible excipient selected from the group consisting of glycerin, mineral oil, polycarbophil, carbomer 934P, hydrogenated palm oil, glyceride, sodium hydroxide, sorbic acid, TWEEN 80, and purified water.

One preferred formulation of the invention comprises 75% of ethoxylated fatty glycerides, such as SUPPOCIRE® AS2, 10% hydroxypropyl methylcellulose, and 15% ethoxydiglycol.

E. Pharmaceutical Agents

Compositions of the invention are suitable for transmucosal delivery of any drug which asserts a therapeutic effect when delivered to the systemic circulation through the vaginal, nasal or buccal mucosa. Based on the specific properties of non-ionizable glycol derivatives, drugs suitable for delivery by this invention are polar compounds having an octanol/water partition coefficient smaller than 2.5 (log p>2.5).

Representative of these drugs are groups of anti-inflammatory agents, calcium or potassium channel antagonists, β-adrenergic agonists, vasodilators, COX-1 and/or COX-2 inhibitors, antibacterial, antiviral, antipsychotic, antifungal, anti-osteoporotic, anti-migraine, anti-HIV, anti-cancer agents and native or biotechnology-derived pharmaceutically active agents, such as proteins and peptides.

Non-limiting representative examples of these drugs are nonsteroidal anti-inflammatory drugs which include aspirin, ibuprofen, indomethacin, phenylbutazone, bromfenac, fenamate, sulindac, nabumetone, ketorolac, and naproxen.

Examples of calcium channel antagonists include diltiazem, israpidine, nimodipine, felodipine, verapamil, nifedipine, nicardipine, and bepridil.

Examples of potassium channel blockers include dofetilide, almokalant, sematilide, ambasilide, azimilide, tedisamil, sotalol, piroxicam, and ibutilide.

Examples of β-adrenergic agonists include terbutaline, salbutamol, metaproterenol, and ritodrine.

Vasodilators include nitroglycerin, isosorbide dinitrate and isosorbide mononitrate.

Examples of COX-2 and COX-1 inhibitors are naproxen, ketoprofen, ketorolac, indomethacin, diclofenac, tenoxicam, celecoxib, meloxicam and flosulide.

Examples of anti-osteoporotic drugs are bisphosphonates selected from the group consisting of alendronate, clodronate, etidronate, pamidronate, tiludronate, ibandronate, zoledronate, olpadronate, residronate and neridronate suitable for prevention and treatment of osteoporosis, Paget's disease, other diseases of bone and skeleton and cancer.

Examples of antifungal, antibacterial or antiviral drugs are miconazole, terconazole, isoconazole, fenticonazole, fluconazole, nystatin, ketoconazole, clotrimazole, butoconazole, econazole, metronidazole, clindamycin, 5-fluoracil, acyclovir, AZT, famovir, ribavirin, penicillin, tetracycline and erythromycin.

Examples of anti-migraine drugs are almotriptan, eletriptan, flovatriptan, naratriptan, rizatriptan, sumatriptan, zolmitriptan, ergotamine, dihydroergotamine, bosentan and lanepitant.

Examples of anti-cancer drugs are vincristine, cisplastin, doxorubicin, daunorubicin, etoposide, topotecan, irinotecan, paclitaxel, docetaxel, cyclophosphamide, methotrexate, and gemcitabine.

Examples of anti-HIV drugs are saquinavir, ritonavir, indinavir, amprenavir, nelfinavir, lopinavir and ganciclovir.

Examples of biotechnology-derived drugs are insulin, calcitonin, vasopressin, luprolide, somatostatin, oxytocin, bivalirudin, integrilin, natrecor, abarelix, gastrine G17, peptide, ziconotide, cereport, interleukin, humanized antibodies and growth hormone.

Composition of the invention is thus consisting essentially of a combination of an effective amount of a pharmaceutical agent selected from the group of drugs exemplarily listed above or any other drug suitable for transmucosal delivery in combination with at least one non-ionizable glycol derivative, and further optionally in combination with one or several other penetration enhancers and/or lipophilic or hydrophilic carrier vehicle and/or mucoadhesive agent and/or additional nontoxic pharmaceutically acceptable biocompatible excipient.

Said composition is typically formulated as a bioadhesive tablet, bioadhesive microparticle, microemulsion, cream, lotion, foam, ointment, paste, solution, suspension and gel for nasal, buccal or transvaginal delivery and as a vaginal suppository for transmucosal vaginal delivery, said composition optionally incorporated into a nasal, buccal or vaginal device.

II. Transmucosal Drug Delivery

Transmucosal drug delivery permits transport of the drug into the systemic circulation directly through the nasal, buccal and vaginal mucosa, thereby avoiding invasive intravenous or less effective oral administration.

Administration of drug via the oral route is achieved through intestinal mucosa. The drug so absorbed is transported into and by the intestinal venous drainage to the porta hepaticus to be initially processed by the liver. Since the liver is a body detoxifying system, large portion of the drug is either transformed or metabolized by the liver prior to reaching the systemic circulation. The drug is thus subjected to so called first pass effect wherein typically a large portion of the drug is lost or deactivated.

The oral route, although very convenient for a subject, is thus not very effective and results in great loss of the drug and/or in undesirable effects caused by the large amount of drug or by its metabolites.

Administration of substances via the intravenous route, transdermally, that is through the skin, or through the vaginal, nasal and buccal mucosal barriers avoids the above mentioned first pass effect and permits direct drug delivery to the systemic circulation without being initially metabolized by the liver.

The intravenous route of administration is invasive and inconvenient. Topical transdermal drug delivery through the skin has been utilized for a long time now but it has its problem with dosing, with bioavailability, with drug deactivation by light, humidity or heat, and with transfer through and crossing of a dermal barrier.

The current invention is based on prior discovery that drug formulated in certain fashion can promote penetration and crossing of the mucosal barrier if a sufficient amount of a non-ionizable glycol derivative is present in a transmucosal composition.

Such compositions are useful for delivery of drugs by permeation through the vaginal, nasal or buccal mucosa directly to the systemic circulation. The glycol derivative essentially present in these compositions enhances permeation through the mucosa of the drug which would otherwise not be able to cross the mucosal barrier.

Moreover, the drug compounds solubilized with a glycol derivative in combination with an appropriate mucoadhesive agent allow a prolonged contact of the drug with the mucosal surface, thereby further enhancing the efficiency of delivery of the compound.

The penetration enhancing effect of the glycol derivative is further enhanced by the use of a carrier, such as a lipophilic or hydrophilic carrier, and/or by use of mucoadhesive agents described above.

A. Toxicology Study of Repeated Dose of Transmucosal Drug Delivery

The compositions and methods described herein are safe, efficacious and suitable for repeated transvaginal administration of the pharmaceutically active agent using alendronate as a representative drug as shown in the study described below.

A 10 day, repeat dose, vaginal toxicity study was conducted in healthy female rabbits. Three doses and two controls were used. The rabbits were dosed daily with suppositories containing either 0.013 mg, 0.13 or 0.3 mg of alendronate. This corresponds to human doses of 0.3, 3 and 30 mg/70 kg of alendronate in humans. Doses of SUPPOCIRE® and SUPPOCIRE® plus ethoxydiglycol were used as controls. The study findings are summarized below.

TABLE 1

Rabbit Doses and Corresponding Human Doses

| Rabbit Dose | Corresponding Human Dose |
| --- | --- |
| 0.013 mg | 0.3 mg |
| 0.13 mg | 3 mg |
| 1.3 mg | 30 mg |

The NOEL is 0.013 mg/3 kg rabbit dose which is the equivalent 0.3 mg dose in a 70 kg human. Mild erythema of the external portion of the vagina was noted in days 7-10 in the 0.13 and the 1.3 mg dose groups.

Mild erythema in the mid-portion of the vagina was noted microscopically for the 0.13 mg dose group (mid-dose, equivalent of 3 mg in humans).

Erythema and inflammation was noted microscopically in the mid-portion of the vagina for the 1.3 mg (high dose, equivalent of 30 mg in humans) dose group.

No erythema, inflammation or erosion was noted on the cervix or uterus for any of the dose groups.

The controls exhibited no macroscopic or microscopic effects. Transvaginally administered alendronate exhibited no systemic side effects at any dose tested.

The results from toxicology support a one-time vaginal dose of alendronate in humans up to and including a 3 mg dose. The data can be extrapolated to indicate that a one-time 10 mg human dose is also safe. Vaginal dosing of ethoxydiglycol at the levels suitable for the Phase I clinical study has no toxicological effect.

The criteria for stopping the human study includes the presence of ulceration of the vaginal tissue. Because the rabbit toxicology testing translates to humans, even after the consecutive 10-day dosing of the highest dose (equivalent of 30 mg human dose), the results described above show that this dose and this rate of administration is clinically safe for use in humans.

B. Vaginal Transmucosal Drug Delivery

Vaginal transmucosal delivery of a pharmaceutical agents was investigated in the rabbit model. A bisphosphonate alendronate was selected as a representative drug because a systemic bioavailability following the oral or intravenous administration was previously studied and its i.v. and oral levels were determined. Toxicologic studies show these levels to be safe as described above. When administered orally in essentially the same amount, the systemic level of alendronate is generally below 1% compared to i.v. administration.

The objective of this study was to determine whether the delivery of alendronate across the vaginal mucosa has the potential to significantly improve the systemic bioavailability of this drug against the oral delivery and whether the bioavailability of such transmucosal delivery would be comparable to the bioavailability achieved with intravenous delivery.

Figure 1:
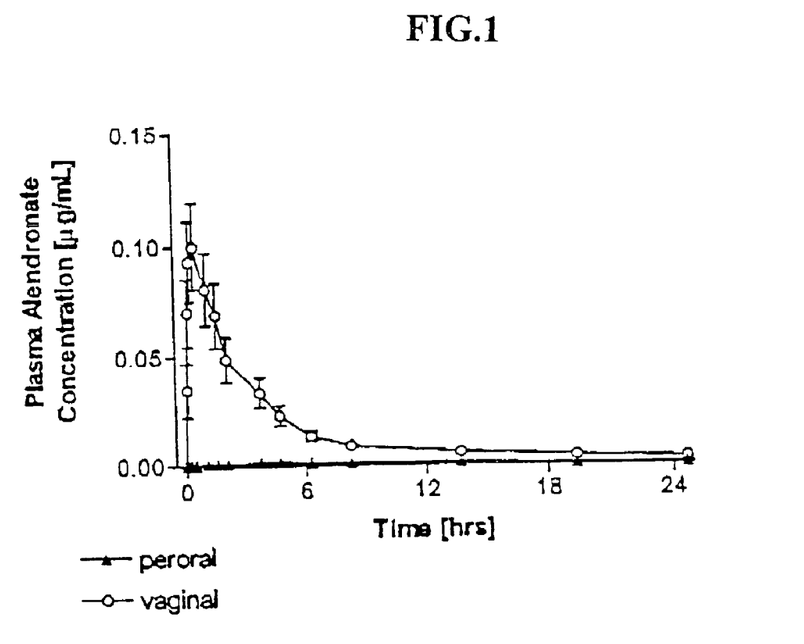
FIG. 1 illustrates concentrations-time profiles of alendronate in plasma (μg/ml) following oral and vaginal administration of a single dose of alendronate to female white New Zealand rabbit.
Figure 2:
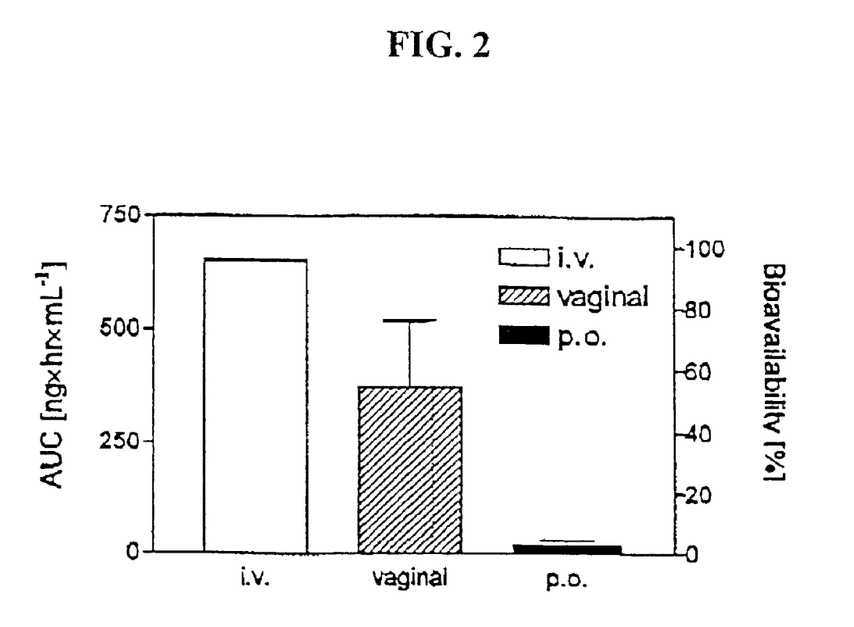
FIG. 2 is a graph representing bioavailability, in percent, of alendronate in plasma following an oral, intravenous or vaginal administration of alendronate to female white New Zealand rabbit.

Plasma pharmacokinetics of alendronate were determined in anesthetized female white New Zealand rabbits after intravenous, vaginal, and peroral administration (dose=0.15, 0.14 and 0.22 mg/kg, respectively). For analytical purposes, each dose was supplemented with a trace amount of [$^{14}$C]alendronate. Model-independent pharmacokinetic parameters were calculated using WinNonlin form plasma concentrations of alendronate collected for 24 hours. Results are illustrated in FIGS. 1 and 2 and in Table 2.

TABLE 2

Pharmacokinetic Parameters of Alendronate in New Zealand Rabbits Following Intravenous, Vaginal, and Peroral Administration

| Parameter | Intravenous | Vaginal | Peroral |
|---|---|---|---|
| Dose [mg × kg$^{-1}$] | 0.15 | 0.14 | 0.22 |
| $c_{max}$ [ng × mL$^{-1}$] | N/A | 34.0 ± 14.4 | 1.8 ± 1.2 |
| $t_{max}$ [hr] | N/A | 0.5 ± 0.1 | 4.8 ± 2.0 |
| AUC [ng × hr × mL$^{-1}$] | 652.7 | 180.0 ± 82.4 | 18.2 ± 12.1 |
| $t_{1/2}$ [hr] | 13.4 | 19.6 ± 3.4 | 17.4 ± 5.1 |
| F | 100 | 30.1 ± 13.4 | 2.0 ± 1.3 |

Pharmacokinetic parameters were calculated from plasma drug concentrations using the model-independent analysis module of WinNonlin.

Table 2 lists pharmacokinetic parameters observed in plasma of White New Zealand rabbits following the intravenous, intravaginal and oral administration of alendronate in doses 0.15 mg/kg for intravenous, 0.14 mg/kg for vaginal and 0.22 mg/kg for oral route of administration. Table 2 further shows maximal plasma concentration ($c$max), area under the curve (AUC) in ng/hr/ml$^{-1}$, an apparent half-life ($t_{1/2}$/hr) and bioavailability (F).

As seen in Table 2, after intravenous administration of alendronate in a saline solution, alendronate rapidly disappeared from the vascular system with a terminal half-life of 13.4 hours. This is consistent with earlier observations in various other species and relates to the high affinity of this drug to the bone.

When delivered vaginally using a suppository that was formulated with 25% (w/w) TRANSCUTOL®, plasma concentrations of alendronate rapidly increased to reach a maximum around 0.5 hr, as seen in FIG. 1. From the area under the plasma concentration time curve (AUC), the mean absolute bioavailability that was calculated for this new route of administration was 30.1%. The terminal half-life of alendronate following vaginal administration was close to 20 hrs. However, within statistical confidence, this value is not significantly different from the corresponding terminal half-life calculated from the intravenous data.

In comparison, the mean absolute bioavailability of alendronate in rabbits following oral administration was only 2%. This is in agreement with published data for dogs and monkeys.

From these results, it is clear that vaginal delivery of alendronate is significantly more effective than oral delivery. To achieve plasma concentrations of alendronate following vaginal administration that are equivalent to the drug concentrations measured following oral administration, approximately 7% of the oral dose would be sufficient for vaginal administration. As a substantial benefit for the patient, because of the 20-30% increased absorption into the systemic circulation by the vaginal delivery, the intravaginally delivered bisphosphonates may be delivered daily, bi-daily, weekly, monthly or even quarterly. The vaginal administration of alendronate can significantly reduce the severe side effects that are characteristic for the drug class of bisphosphonate.

FIG. 1 shows concentration-time profiles of alendronate in plasma following vaginal and oral administration of a single dose of 0.14 and 0.22 mg/kg, respectively, to a female White New Zealand rabbit. All studies were performed in duplicate and the values given are average±SEM.

As seen from FIG. 1, while peroral administration of 0.22 mg/kg of weight did not raise concentrations (μg/ml) of alendronate in plasma during 24 hours, or such increase was very low and occurred only during the first six hours, resulting in only about 2% bioavailability of alendronate, the vaginal administration resulted in rapid increase of alendronate in plasma, reaching its peak in less than one hour after administration and decreasing slowly during 24 hours, reaching bioavailability values of about 30%. About fifteen times more alendronate was present and available in plasma following the vaginal delivery when compared to the levels of alendronate observed following the orally administered alendronate.

These results are unexpected and surprising and confirm that the vaginal delivery is efficacious and combined with elimination of adverse reactions observed during oral delivery, the vaginal delivery is much better way to administer bisphosphonates.

FIG. 2 is a graphical illustration of bioavailability (%) of alendronate observed following the oral (2%), vaginal (30%) and intravenous (set to be 100%) administration of alendronate in 0.22, 0.14 and 0.15 mg/kg doses, respectively.

As seen from the above results, the vaginal delivery is clearly superior to the oral delivery and eliminates all adverse effects accompanying the oral administration. Because of the unique formulation consisting of the mucoadhesive agents, penetration promoters and a drug specific carrier, the poor absorbance through the gastrointestinal (GI) tract mucosa is overcome and the bisphosphonate is delivered in a therapeutically effective amount through the vaginal mucosa directly to the systemic circulation.

According to the invention, bisphosphonates which are brought into contact with the vaginal mucosa and epithelium of a female increase the drug bioavailability. The method for transmucosal delivery of drugs is eminently suitable for delivery of drugs into the systemic blood circulation for treatment of various diseases.

C. Buccal or Nasal Transmucosal Drug Delivery

Buccal and nasal transmucosal drug delivery was studied on porcine buccal or nasal epithelium using procedure described in Example 11. Results of these studies is shown in FIGS. 3 and 4.

Figure 3:
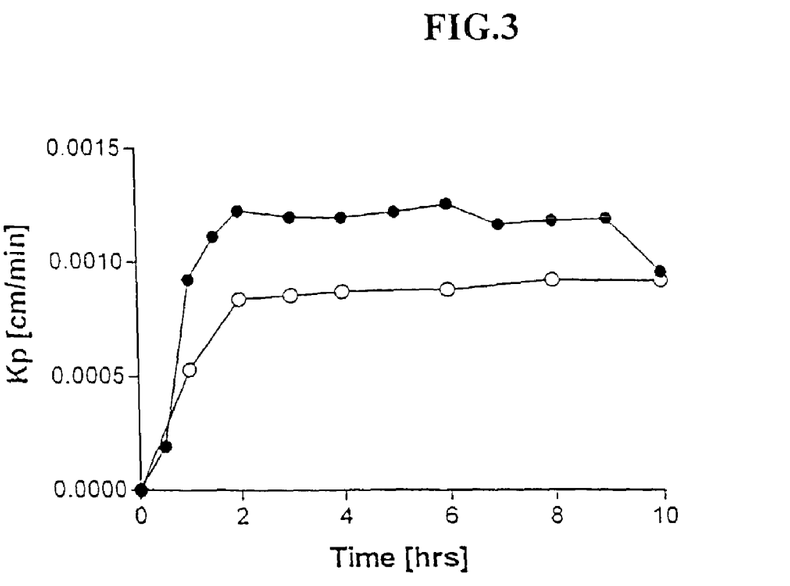
FIG. 3 is a graph showing a transepithelial transport of [$^3$H]water across porcine buccal mucosa in vitro. Water flux was determined in the presence (●) and absence (○) of 30% (v/v) using a continuous flow apparatus. Mean flux at each time point is represented (n=7). Results were statistically analyzed using one-way ANOVA ($p \leq 0.05$).

Results obtained in the study of the buccal transmucosal delivery are shown in FIG. 3. FIG. 3 illustrates transepithelial transport of [$^3$H]water across porcine buccal mucosa in vitro. For this study, water flux was determined in the presence (●) and absence (○) of 30% (v/v) TRANSCUTOL® using a continuous flow apparatus. Mean flux at each time point is represented (n=7). Results were statistically analyzed using one-way ANOVA (p<0.05).

Transepithelial flux of water across porcine buccal epithelium reaches steady state after a lag time of approximately 2 hrs (FIG. 3). These results confirm the maintenance of effective barrier properties of the mucosa in this in vitro model. This is consistent with earlier findings published in the literature. Addition of 30% (v/v) of TRANSCUTOL® significantly increased the flux of the marker solute across the buccal mucosa. The mean steady state Kp value determined in the presence of this permeation enhancers was ~25% increased as compared to control (Kp=1.11±0.01×10$^{-3}$ cm/min vs. 0.90±0.01×10$^{-3}$ cm/min). As a consequence, TRANSCUTOL® appears to modify the keratinized epithelial barrier properties and allows hydrophilic molecule to permeate into deeper tissue layers. From a drug delivery viewpoint, this implies that TRANSCUTOL® acts as an efficient permeation enhancer to promote transfer of pharmacologically active molecules across the buccal mucosa.

Figure 4:
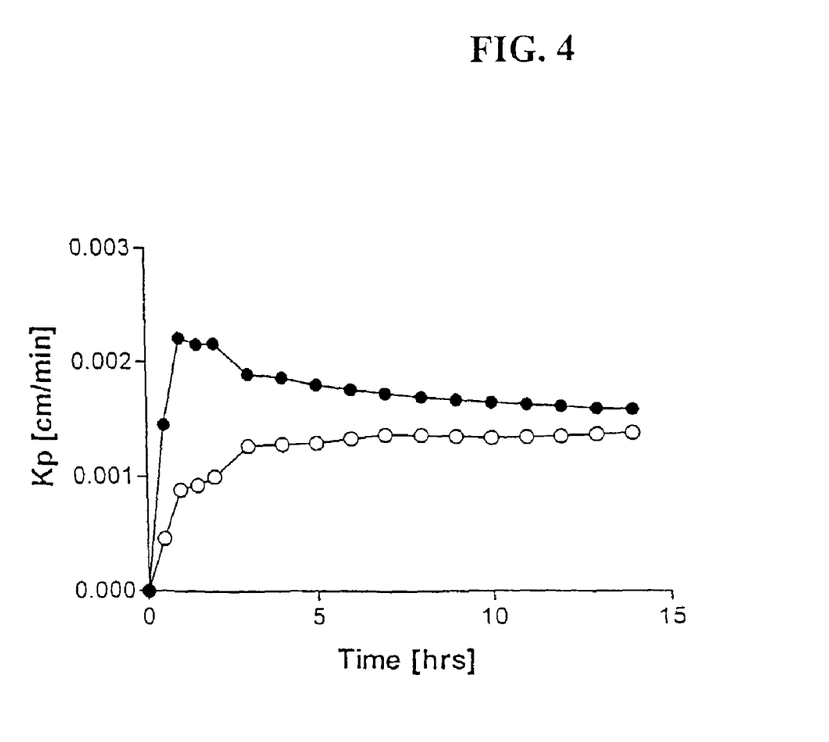
FIG. 4 is a graph showing a transepithelial transport of [$^3$H]water across porcine nasal mucosa in vitro. Water flux was determined in the presence (●) and absence (○) of 15% (v/v) TRANSCUTOL® using a continuous flow apparatus. Mean flux at each time point is represented (n=7). Results were statistically analyzed using one-way ANOVA ($p \leq 0.05$).

Studies for determination of transmucosal nasal drug delivery are illustrated in FIG. 4. FIG. 4 shows transepithelial transport of [$^3$H]water across porcine nasal mucosa in vitro. Water flux across the nasal mucosa was determined in the presence (●) and absence (○) of 15% (v/v) TRANSCUTOL® using a continuous flow apparatus. Mean flux at each time point is represented (n=7). Results were statistically analyzed using one-way ANOVA (p<0.05).

Similarly to the results obtained for buccal transmucosal delivery, such nasal transmucosal delivery was enhanced in the presence of the permeation enhancer TRANSCUTOL®. As shown in FIG. 4, TRANSCUTOL® significantly increased water flux across the nasal mucosa. Steady state flux of the marker solute across this non-keratinized epithelial barrier was reached after a comparable lag time of 3 hrs. However, the potency of TRANSCUTOL® to increase transepithelial transport of this small, hydrophilic solute was significantly greater in the nasal mucosa than in the buccal mucosa. The mean steady state Kp value of water determined across porcine nasal mucosa in the presence of 15% (v/v) TRANSCUTOL® increased by ~37% when compared to control PBS (Kp=1.83±0.02×10$^{-3}$ cm/min vs. 1.33±0.04×10$^{-3}$ cm/min). This implies that the barrier properties of this in vitro model of the nasal mucosa are more sensitive to changes induced by the permeation enhancer TRANSCUTOL®. Furthermore, the increased water flux under control conditions in PBS across the nasal mucosa versus the corresponding data obtained using buccal mucosa support the conclusion that the barrier properties of the nasal mucosa represents an epithelial barrier with a greater intrinsic permeability than the buccal mucosa. This conclusion is consistent with the physiological role of these tissues.

D. Formulations and Devices

The composition of the invention is formulated for its specific use. Thus, for nasal transmucosal administration, the composition is formulated as a solution, suspension, cream, ointment, spray, foam, paste or gel. For buccal transmucosal delivery, the composition is formulated as a tablet, capsule, foam, paste, gel, or spray or is microincorporated into a device insertable into the buccal space, such as a patch, strip, permeable pad or bag, etc. For vaginal transmucosal delivery, the composition is formulated as tablet, paste, bioadhesive tablet, bioadhesive microparticles, microemulsion, cream, lotion, foam, paste, ointment, or gel. Each of these may be conveniently incorporated into an intravaginal device, such as, for example, a tampon, vaginal ring, pessary, suppository or vaginal sponge.

Bioadhesive tablets consist essentially of hydroxypropyl cellulose and polyacrylic acid. These tablets release drugs for up to five days once they are placed in an appropriate formulation.

Bioadhesive microparticles constitute still another drug delivery system suitable for use in the present invention. This system is a multi-phase liquid or semi-solid preparation which does not seep or leak from the vagina, nasal or buccal cavity as do most current suppository formulations. The bioadhesive microparticles cling to the wall of nasal or buccal cavity or from the vagina and release the drug over a several hour period of time. Many of these systems were actually designed for treatment of nasal tissue (e.g. U.S. Pat. No. 4,756,907), but not for transmucosal delivery through nasal mucosa.

The system according to the invention may further comprise microspheres containing an active drug and a penetration enhancer or sorption promoter for enhancing transmucosal delivery of the drug. The microparticles have a diameter of 10-100 µm and can be prepared from starch, gelatin, albumin, collagen, or dextran.

For all these transmucosal administrations, the drug can also be incorporated into solutions, suspensions, creams, lotions, foams, pastes, ointments, and gels which can be applied to the nasal or buccal cavity or vagina, for example, by using an applicator.

Processes for preparing pharmaceuticals in cream, lotion, spray, foam, paste, ointment, tablet and gel form can be found throughout the literature. An example of suitable system is a standard lotion formulation containing glycerol, ceramides, mineral oil, petrolatum, parabens, fragrance and water. Other suitable nontoxic pharmaceutically acceptable formulations for use in the transmucosal administration of the present invention will be apparent to those skilled in the art of pharmaceutical formulations and examples are described in REMINGTON'S PHARMACEUTICAL SCIENCES, 19$^{th}$ Edition, A. R. Gennaro, ed., 1995.

The choice of additional suitable excipient depends on the exact nature of the particular transmucosal delivery route and the form in which the drug is delivered. Thus, the actual formulation depends on whether the active ingredient(s) is/are to be formulated into a cream, lotion, foam, ointment, paste, solution, or gel, or whether it will be incorporated into an appropriate device for transmucosal delivery, as well as on the identity of the active ingredient(s).

III. Cryoprotection

Non-ionizable glycol derivatives of the invention are further suitable for long-term protection of cells, tissue, organs and embryos.

The derivative of the invention, preferably ethoxydiglycol is also useful for cryoprotection as a permeation enhancer which effectively displaces the water or another acqueous-fraction from the cell and allow ethoxydiglycol to act as a cryoprotectant. Ethoxydiglycol may be used alone or in combination with other solvents such as propanediol.

EXAMPLE 1

Preparation of Medicated Vaginal Suppository for Transmucosal Delivery

This example describes the preparation of transmucosal composition containing a hydrophilic or lipophilic pharmaceutical agent for transmucosal delivery.

The dose of the hydrophilic drug between 0.001-2000 µg/kg was determined. Radioactively labeled equivalent (4-7 µCi) was added to the unlabeled compound. Vaginal suppositories utilized the lipophilic carrier were formulated and prepared 24 hours prior to each experiment.

The three basic ingredients for the suppositories were SUPPOCIRE® AS2 (Gattefosse, Westwood, N.J.) (75% wt), a mucoadhesive agent, hydroxypropyl methylcellulose, specifically METHOCEL® K, HPMC K15M, commercially available from Dow Chemical, Midland, Mich. (10% wt), and ethoxy diglycol obtained from Gattefosse (15% wt).

To make eight suppositories, 4.5 grams of SUPPOCIRE, 600 mg of HPMC, 900 mg of ethoxydiglycol, and the calculated dose of the drug, and its labeled counterpart were weighed out. SUPPOCIRE was melted in a disposable 100 mL polypropylene beaker suspended in water at 50° C. The solution was stirred until completely melted. HPMC and ethoxydiglycol were then added and mixed. Finally, the unlabeled drug and the radioactively-labeled drug were added to the warm solution. The warm mixture was poured into TYGON® tubing molds (2 cm lengths). The tubing was kept upright on an ice-cold glass slab. Suppositories were kept refrigerated until use. The actual drug dose was determined by comparison of the weight of the drug containing suppository with suppository without the drug.

The lipophilic drug is formulated into a suppository in the same way except that the lipophilic carrier is substituted with the hydrophilic carrier.

EXAMPLE 2

Preparation of Verapamil Containing Vaginal Suppository for Transmucosal Delivery This example describes the preparation of transmucosal composition containing verapamil for transmucosal vaginal delivery.

The dose of verapamil (Sigma/Aldrich, St. Louis, Mo.) was 0.15-0.6 mg/kg body weight. Radioactively labeled verapamil (4-7 μCi) was added to the unlabeled compound. Vaginal suppositories were formulated and prepared 24 hours prior to each experiment. The three basic ingredients for the suppositories were SUPPOCIRE® AS2 (Gattefosse, Westwood, N.J.) (75% wt), hydroxypropyl methylcellulose, specifically METHOCEL® K, HPMC K15M commercially available from Dow Chemical, Midland, Mich. (10% wt) and ethoxydiglycol obtained from Gattefosse (15% wt).

To make eight suppositories, 4.5 grams of SUPPOCIRE, 600 mg of HPMC, 900 mg of ethoxydiglycol, and the calculated dose of the drug, and its labeled counterpart were weighed out. SUPPOCIRE was melted in a disposable 100 mL polypropylene beaker suspended in water at 50° C. The solution was stirred until completely melted. HPMC and ethoxydiglycol were then added and mixed. Finally, the unlabeled drug and the radioactively-labeled drug were added to the warm solution. The warm mixture was quickly poured into TYGON® tubing molds commercially available from Fisher Scientific, Pittsburgh, Pa. (2 cm lengths), the tubing was kept upright on an ice-cold glass slab. Suppositories were kept refrigerated until use. The suppository was weighed prior to each experiment to determine the actual drug dose.

EXAMPLE 3

Preparation of Vaginal Suppositories

This example describes the preparation of intravaginal suppositories for transmucosal delivery of various drugs.

A vaginal suppository is prepared according to Example 1 for transmucosal administration of each one of the following drugs at the indicated dose: aspirin (975 mg), piroxicam (20 mg), indomethacin (50 mg), fenamate (500 mg), sulindac (200 mg), nabumetone (750 mg), detorolac (10 mg), ibuprofen (200 mg), phenylbutazone (50 mg), bromfenac (50 mg), naproxen (550 mg), lidocaine (100 mg), mepivacaine (0.2 mg), etidocaine (200 mg), bupivacaine (100 mg), 2-chloroprocaine hydrochloride (100 mg), procaine (200 mg), tetracaine hydrochloride (20 mg), diltiazem (60 mg), israpidine (10 mg), nimodipine (30 mg), felodipine (450 mg), nifedipine (90 mg), nicardipine (30 mg), ritodrine (150 mg), bepridil (300 mg), dofetilide (1 mg), almokalant (1 mg), sematilide (1 mg), ambasilide (1 mg), azimilide (1 mg), tedisamil (100 mg), sotalol (240 mg), ibutilide (1 mg), terbutaline (5 mg), salbutamol (1 mg), piroxicam (20 mg), metaproterenol sulphate (20 mg), nitroglycerin (3 mg), isosorbide dinitrate (40 mg), isosorbide mononitrate (120 mg). Other pharmaceutically active agents, as listed above, in appropriate amounts, are formulated in the same way.

All of the steps in the preparation of the drug suppository are identical to those of Example 1 or 2 except that no radiolabeled compound is used, the amount of ethoxydiglycol is varied from 0.01-60% by weight, depending on the drug properties and characteristics and the indicated amount of the drug is used in place of verapamil.

The quantity of the drug dosage needed to deliver the desired dose depends on the concentration of the active ingredient in the composition and the amount of the non-ionizable glycol derivative acting as a penetration enhancer. The therapeutic dosage range for vaginal transmucosal administration of the compositions of the present invention will vary with the size of the patient.

EXAMPLE 4

Preparation of a Solution Containing Naproxen for Transmucosal Nasal Delivery

This example describes the preparation of transmucosal and ethoxydiglycol (15% wt) containing nasal composition.

120 mg of naproxen is combined with 10 mg of Tween 80. That mixture is then combined with a quantity of isotonic saline sufficient to bring the total volume of the solution to 50 mL. The solution is sterilized by being passed through a 0.2 micron Millipore filter.

EXAMPLE 5

Preparation of a Transmucosal Gel Composition Containing Ketorolac

This example describes the preparation of transmucosal gel composition containing ketorolac for transvaginal delivery.

250 mL of isotonic saline is heated to 80° C. and 1.50 grams of hydroxypropyl methylcellulose (METHOCEL®) and ethoxydiglycol (15% wt) are added, with stirring. The resultant mixture is allowed to stand at room temperature for 2 hours. Then 120 mg of ketorolac is mixed together with 10 mg of Tween 80. The ketorolac/Tween mixture and a quantity of isotonic saline sufficient to bring the total volume to 500 mL were added to the gel and thoroughly mixed.

EXAMPLE 6

Preparation of Transmucosal Composition Containing Ibuprofen for Vaginal Application This example describes the preparation of transmucosal vaginal gel for transmucosal delivery containing ibuprofen.

Ibuprofen (I-4883, Sigma/Aldrich, St. Louis, Mo.) (200 mg) is added to one mL of gel comprised of the following ingredients: glycerin, mineral oil, polycarbophil, carbomer 934P, hydrogenated palm oil, glyceride, sodium hydroxide, sorbic acid, and purified water.

EXAMPLE 7

Preparation of Vaginal Medicated Tampons

This example describes the preparation of transmucosal vaginal composition incorporated into a tampon.

The drugs listed in Example 3 are added to the tampon as powders, solutions, suspension or emulsions either before the tampon is fabricated or the prefabricated tampons are soaked in the solution, suspension, emulsion or other fluid preparation containing the drug.

The amount of the drug is such that it assures that the dose administered by vaginal tampon is at least as high as the one indicated in Example 3 and is delivered transvaginally in a dose linear manner.

EXAMPLE 8

Preparation of Drug Containing Vaginal Tampon Device for Transvaginal Delivery This example describes a process for preparation of tampon containing a composition formulated as suppository incorporated into said tampon for transvaginal delivery of paclitaxel.

Paclitaxel, obtained from Samyang Genex, KO was mixed with radioactively labeled $^3$H paclitaxel (4-7 µCi). Vaginal suppositories were formulated and prepared 24 hours prior to each use.

The three basic ingredients for the paclitaxel formulation were the carrier PEG 3350 obtained from Fisher Scientific, Pittsburgh, Pa. (75%/wt), a mucoadhesive hydroxypropyl methylcellulose (e.g. METHOCEL® K, HPMC K15M) obtained from Dow Chemical, Midland, Mich., (10%/wt), and penetration enhancer ethoxydiglycol obtained from Gattefosse (15%/wt).

These ingredients were mixed in percent amounts as shown. To make eight suppositories, 4.5 grams of PEG, 600 mg of HPMC, 900 mg of ethoxydiglycol, the calculated dose of the drug (250 mg/suppository), and its labeled counterpart were weighed out. PEG 3350 was melted in a disposable 100 mL polypropylene beaker suspended in water at 60° C. The solution was stirred until completely melted. HPMC was then added and mixed. Finally, the unlabeled drug was dissolved in ethoxydiglycol and added to the warm suspension.

The warm mixture was quickly poured into TYGON tubing molds (2×0.5 cm dimensions), the tubing was kept upright on an ice-cold glass slab. Suppositories were kept refrigerated until use. The suppository was weighed prior to and following each experiment to determine the actual drug dose.

The prepared suppository was then incorporated into a vaginal tampon in such a way that the drug was released from the tip of the suppository in a sustained time-release manner.

In an alternative arrangement, the tampon was soaked in the formulation comprising paclitaxel, dried and protected by the carton inserter until used.

EXAMPLE 9

Preparation of Pamidronate Containing Buccal Pad

This example describes preparation of pamidronate containing buccal pad.

The dose of unlabeled pamidronate, commercially available from Sigma, St. Louis, Mo., was 0.2 mg/kg body weight. The pamidronate buccal pad is prepared by soaking the cotton, hydroxypropyl methyl cellulose or foam pad in the solution of pamidronate prepared similarly as described in Example 4.

EXAMPLE 10

Alendronate Pharmacokinetic Studies

This example describes procedures used for pharmacokinetic studies for alendronate intravaginal and transvaginal delivery.

$^3$H-Alendronate was obtained from DuPont/NEN, Boston, Mass. Prior to intravenous injection, unlabeled alendronate (Sigma/Aldrich, St. Louis, Mo.) (0.15-0.6 mg/kg body weight, i.v.) was dissolved in 0.5 mL dimethyl sulfoxide (Syntex, West Des Moines, Iowa). Labeled alendronate (4-7 µCi) was then added to the cold compound just prior to i.v. injection.

Female white New Zealand rabbits weighing 2.8 to 3.5 kg were obtained from Myrtle Rabbitry (Thompson Station, Tenn.). Rabbits were kept in a National Institutes of Health approved facility and were acclimated to their environment at least 48 hours prior to each experiment.

Drug pharmacokinetic studies were performed via both the intravenous, oral and transvaginal modes of administration. During the first series of experiments, the intravenous route of administration was utilized to determine the initial half-lives of the experimental compound. In the second series of experiments, the intravenous and transvaginal routes of administration were compared in the same rabbit.

For the half-life experiments, after an 18 hour overnight fast, each rabbit was premedicated with ketamine (35 mg/kg, i.m.), xylazine (5 mg/kg, i.m.), and atropine (0.5 mg, i.m.). Each rabbit was intubated and anesthesia was maintained with isoflurane (1-3%). Vital signs were monitored throughout the experiment via a pulse oximeter. Rabbit body temperature was kept constant by a recirculating heating pad. Intravenous access was achieved by placement of a 22 gauge TEFLON catheter in the peripheral ear vein. Intra-arterial access was achieved by placement of a 22 gauge TEFLON catheter in the central artery in the ear. A heat lamp was used to warm the ears to promote peripheral blood flow.

After the rabbit was anesthetized, the mixture containing labeled and unlabeled drug was injected through the ear vein over a 10 second to 2 minute period. Blood samples were drawn through the arterial line at 0.1, 0.25, 0.5, 0.75, 2, 4, 6, 8, 10, 12 and 24 hours relative to the time of injection. Blood samples (1 mL) were placed in a polypropylene tube containing EDTA. The blood was centrifuged at 2000 rpm for 10 minutes and 0.5 mL of plasma was placed into a scintillation vial.

Solvable tissue solubilizer 0.5 mL (Packard, Meridian, Conn.) was added to the plasma samples and samples were vortexed for 30 seconds. 10 mL of Hionic-Fluor scintillation cocktail (Packard) was added and samples were vortexed for 1 minute before they were placed on the scintillation counter.

For the transvaginal experiments, vaginal suppositories were formulated and kept on ice. The suppository was introduced into the rabbit vagina using the barrel of a plastic transfer pipette (Baxter, McGaw Park, Ill.) and a tuberculin syringe as the plunger to load the suppository into the vagina to a depth of 7 to 8 cm. Blood samples were taken at 0.1, 0.25, 0.5, 0.75, 2, 4, 6, 8, 14, 20 and 25 hours relative to suppository administration.

The rabbit was allowed to recover and a 7-day washout period was carried out prior to the vaginal administration.

Alendronate was administered as described above and also orally. As shown in Table 2 above, plasma levels of alendronate administered intra and transvaginally were fifteen times as high as those observed after oral administration and persisted for a prolonged period of time.

EXAMPLE 11

Transmucosal Drug Delivery Through Nasal or Buccal Mucosa

This example describes procedures used for determination of transmucosal drug delivery through a nasal or buccal mucosa.

Porcine buccal and nasal mucosa (lateral) was obtained at slaughter and utilized within 3 hours of harvest. Tissue samples approximately 8 mm in diameter were mounted between two halves of through-flow mucosal perfusion cells exposing an area of epithelial surface approximately 0.20 cm$^2$ for transepithelial transport. The chambers were mounted on water-jacketed blocks maintained at 37° C. During the set up period, the exposed epithelial surface was kept moist with phosphate buffered saline (PBS, 0.01M, pH 7.4). The buffer solution was removed by vacuum immediately prior to application of labeled test compound.

Transport experiments were initiated by applying 100 μL of a formulation prepared with [$^3$H]-labeled water and 15-30% (v/v) of TRANSCUTOL® onto the epithelial surface using either a pipette (liquid or non-viscous formulations) or a 1 cc syringes (viscous formulations). In general, labeled marker solutes were prepared at a concentration of 1 μCi per dose and remained on the epithelial donor surface for the entire collection period.

In the receiver compartment, PBS was continuously pumped through the lower chamber (i.e., blood compartment) as a collection fluid at rate of 1.8 mL/hr, which was previously determined to be sufficient to maintain sink conditions in the receiver compartment. This fluid was collected into scintillation vials for 1 or 2 hour intervals over the entire collection period and radioactivity was determined by liquid scintillation counter.

Transepithelial flux of the marker solute in the presence of various concentrations of permeation enhancers was calculated at each sampling interval from the relationship: Flux=Q/At where Q is the finite quantity of solute traversing the tissue barrier (dpm) in time t (min); A is the area of epithelial surface exposed in cm$^2$. Steady state flux (J) was determined when no statistically significant differences were found between at least two consecutive time intervals. The permeability constant (Kp) was calculated from the relationship Kp=J/C, where C is the average concentration gradients expressed in dpm/cm$^3$.

Steady state flux values obtained for each solute in the presence of a selected permeation enhancer were statistically compared using one-way analysis of variance (ANOVA) with Tukey post hoc test to identify values significantly different a $p<0.05$.

What is claimed is:

1. A composition for transmucosal delivery of a pharmacologically active agent to a systemic circulation through a vaginal, nasal or buccal mucosa, said composition consisting essentially of said pharmacologically active agent, a non-ionizable glycol ether, a lipophilic or hydrophilic carrier, and a mucoadhesive agent, wherein said pharmacologically active agent is a peptide or protein selected from the group consisting of vasopressin, leuprolide, somatostatin, oxytocin, abarelix, calcitonin, bivalirudin, integrilin, natrecor, gastrin G17, ziconotide, cereport, interleukin and humanized antibodies having a partition coefficient logP<2.5, said agent present in amount from about 0.1 to about 200 mg;

wherein said non-ionizable glycol derivative is selected from the group consisting of ethoxydiglycol, polyoxyethylene lauryl ether, polyoxyethylene monooleyl ether, polyoxyethylene nonylphenol, polyoxyethylene octylphenol ether, polyoxyethylene cholesterol ether, polyoxyethylene soya sterol ether, or a combination thereof, present from about 0.5 to about 25%, by weight;

wherein said lipophilic carrier is a semi-synthetic glycerides of saturated fatty acid of 8-18 carbon chain present from about 60 to about 90%, by weight;

wherein the hydrophilic carrier is a polyethylene glycol of from about 200 to about 8000 molecular weight selected from the group consisting of polyethylene glycol (PEG) 8000, PEG 600, PEG 4000, PEG 3350, PEG 1500, PEG 400, PEG 200 or a mixture thereof present in about 50 to about 90%, by weight;

wherein said mucoadhesive agent is a cellulose derivative, alginate, pectin, polyacrylic acid, hyaluronic acid, polyvinyl alcohol, polyvinyl pyrrolidone, polycarbophil or carbopol present in from about 0.05 to about 25%, by weight.

2. The composition of claim 1 wherein said non-ionizable glycol ether is ethoxydiglycol present in from about 10 to about 20%, by weight.

3. The composition of claim 2 wherein ethoxydiglycol is present in about 15%, by weight.

4. The composition of claim 3 wherein said mucoadhesive agent is hydroxypropyl methylcellulose present in from about 0.05 to about 25%, by weight.

5. The composition of claim 4 wherein said hydroxypropyl methylcellulose is present in from about 0.5 to about 10%, by weight.

6. The composition of claim 5 wherein said pharmacologically active protein or peptide is hydrophilic and said lipophilic carrier is ethoxylated glyceride of saturated fatty acid present in about 75%, by weight.

7. The composition of claim 6 wherein said transmucosal delivery is through nasal or buccal mucosa and wherein said mucoadhesive agent is present from about 0.02 to about 7%, by weight.

8. The composition of claim 5 wherein said pharmacologically active protein or peptide is lipophilic and said hydrophilic carrier is polyethylene glycol from about 200 to about 8000 molecular weight present in about 75%, by weight.

9. The composition of claim 8 wherein said transmucosal delivery is through nasal or buccal mucosa and wherein said mucoadhesive agent is present from about 0.02 to about 7%, by weight.

10. The composition of claim 6 formulated as a bioadhesive system, bioadhesive tablet, bioadhesive microparticle, cream, lotion, foam, paste, ointment, solution, suspension or gel.

11. The composition of claim 10 incorporated into a vaginal ring, vaginal tampon, vaginal pessary, vaginal tablet, vaginal suppository, vaginal sponge, vaginal patch or vaginal strip.

12. The composition of claim 10 incorporated into a nasal or buccal tablet, sponge, pad, patch or strip.

13. The composition of claim 8 formulated as a bioadhesive system, bioadhesive tablet, bioadhesive microparticle, cream, lotion, foam, paste, ointment, solution, suspension or gel.

14. The composition of claim 13 incorporated into a vaginal ring, vaginal tampon, vaginal pessary, vaginal tablet, vaginal suppository, vaginal sponge, vaginal patch or vaginal strip.

15. The composition of claim 13 incorporated into a nasal or buccal tablet, sponge, pad, patch or strip.

16. A composition for transmucosal delivery of a pharmacologically active agent to a systemic circulation through a vaginal, nasal or buccal mucosa, said composition consisting essentially of said pharmacologically active agent, a non-ionizable glycol ether, a lipophilic or hydrophilic carrier, and a mucoadhesive agent, wherein said pharmacologically active agent is a peptide or protein selected from the group consisting of vasopressin, leuprolide, somatostatin, oxytocin, abarelix, calcitonin, bivalirudin, integrilin, natrecor, gastrin G17, ziconotide, cereport, interleukin and humanized antibodies having a partition coefficient logP<2.5, said agent present in amount from about 0.1 to about 200 mg;

wherein said non-ionizable glycol derivative is ethoxydiglycol present from about 0.5 to about 25%, by weight;

wherein said lipophilic carrier is ethoxylated glyceride of saturated fatty acid of 8-18 carbon chain present from about 60 to about 90%, by weight;

wherein the hydrophilic carrier is a polyethylene glycol of from about 200 to about 8000 molecular weight present in about 50 to about 90%, by weight; and wherein said mucoadhesive agent is hydroxypropyl methylcellulose present in from about 0.05 to about 25%, by weight.

17. The composition of claim 16 wherein ethoxydiglycol is present in from about 10 to about 20%, by weight.

18. The composition of claim 17 wherein ethoxydiglycol is present in about 15%, by weight, wherein hydroxypropyl methylcellulose is present in from about 0.5 to about 10%, by weight, wherein when the protein or peptide is hydrophilic said lipophilic carrier is ethoxylated glyceride of saturated fatty acid present in about 75%, by weight, or when the protein or peptide is lipophilic said hydrophilic carrier is polyethylene glycol from about 200 to about 8000 molecular weight present in about 75%, by weight.

19. The composition of claim 18 formulated as a bioadhesive system, bioadhesive tablet, bioadhesive microparticle, cream, lotion, foam, paste, ointment, solution, suspension or gel.

20. The composition of claim 19 incorporated into a vaginal ring, vaginal tampon, vaginal pessary, vaginal tablet, vaginal suppository, vaginal sponge, vaginal patch or vaginal strip.

21. The composition of claim 19 incorporated into a nasal or buccal tablet, sponge, pad, patch or strip.

* * * * *